United States Patent [19]

Price

[11] Patent Number: 4,587,123

[45] Date of Patent: May 6, 1986

[54] COMPOSITIONS AND METHODS FOR REDUCING PEST INFESTATION

[76] Inventor: Jacqueline S. Price, 12706 Califa St., North Hollywood, Calif. 91607

[21] Appl. No.: 625,623

[22] Filed: Jun. 28, 1984

[51] Int. Cl.[4] .................... A01N 65/00; A01N 35/00; A01N 31/00; A01N 27/00; A61K 7/06

[52] U.S. Cl. ................... 424/195.1; 514/693; 514/724; 514/762; 424/70

[58] Field of Search ............... 424/195, 70; 514/693, 514/724, 762

[56] References Cited

U.S. PATENT DOCUMENTS 3,914,406 10/1975 Yankell .............................. 424/44
4,193,986  3/1980 Cox .................................... 424/28

OTHER PUBLICATIONS

Merck Index, 9th ed. 1976, No. 7242.
Chem Abstract 93:2280k, 1980.
Chem Abstr. 86:127288f, 1977.
Chem Abstr. 71:42162a, 1969.

*Primary Examiner*—Jerome D. Goldberg
*Assistant Examiner*—John W. Rollins
*Attorney, Agent, or Firm*—Robert J. Schaap

[57] ABSTRACT

A composition for reducing pest infestation of animals, such as domesticated animals, by topical application of the composition to the animal. The composition is effective in both reducing future infestation by acting as a pest repellent and also acting as a pesticide to aid in also reducing present infestation. The composition comprises a eucalyptus oil, present in an amount of 4% to about 22% by weight, a lower molecular weight, low carbon content alcohol, such as isopropyl alcohol which is miscible with water, present in an amount of about 9% to about 33% by weight, and water generally present in an amount of about 45% to about 85% by weight, all being based on the total fluid weight of the composition. The invention provides a method of reducing pest infestation by topically applying to an animal, on a periodic basis, a selected amount of the pest repellent composition. In addition, the present invention provides a method of improving a shampoo agent by adding to that shampoo agent the composition of the present invention.

24 Claims, No Drawings

COMPOSITIONS AND METHODS FOR REDUCING PEST INFESTATION

BACKGROUND OF THE INVENTION

1. Field of the Invention

This invention relates in general to certain new and useful improvements in compositions and methods of reducing animal pest infestation and more particularly, to compositions and methods of the type stated in which the compositions utilize as primary components, a eucalyptus oil, a low molecular weight, low carbon content alcohol and water.

2. Brief Description of the Prior Art

Most animals, and particularly domesticated animals, are frequently infested with various forms of pests, such as lice, fleas, ticks and the like. This creates an annoyance to the pet owner or pet keeper inasmuch as the animal, such as a dog or a cat, will bring the infesting pests into a household environment and these pests will thereupon attempt to infest themselves in human beings, thereby requiring various forms of commercial pest control.

In an effort to eliminate this problem, many pet owners resort to the use of the so-called "pest control collars", such as the so-called "flea collars" and the like. These collars are not only expensive, but after a period of time, loose significant ability to deter pest infestation.

Other forms of pest control rely upon the use of pest repellent and pesticidal sprays. These sprays usually include chemical compositions which affect the nervous system of the pest. The residue can also act as a repellent and as long as the repellent odor is sufficiently strong the sprayed repellent will repel animal pests. Inasmuch as the prior art repellents quickly lost their repellent odor, the pet owner frequently had to spray the animal with the pest repellent and pesticidal composition in order to maintain any effective repellent and pesticidal activity. In essentially all cases, the flea collars and the pest sprays are an irritant to the animal and often result in sores and other dermal irregularities. Further, the pet owner must use caution in spraying the animal to avoid contact with the nose and mouth of the animal and particularly the eyes and ears of the animal. In addition, and in most cases, the pest spray was also a severe irritant to people and the party using the spray had to avoid direct contact with the same.

There are also many commercially available shampoo agents for washing domesticated animals, such as dogs and cats, and which contain insect pesticides and pest repellents. These commercially available shampoo agents suggest that the shampoo, even when washed from the animal, will leave a residue or at least a smell which is sufficient to repel pests, such as fleas and the like. However, after the shampoo is washed from the animal, the pest repellent and/or pest poisoning ability decreases rapidly with time and in a very short time frame after the shampoo is washed from the animal there remains little or no repellent or pesticidal activity. The commercially available sprays and shampoos all rely upon a pesticidal or repellent residue remaining on the animal coat or skin which provides the repellent or pesticidal activity. As a result these commercial sprays and shampoos become skin irritants and can result in severe skin irritation, if not infection, to the animal.

Notwithstanding the foregoing, generally all commercially available insect repellents of the types used with animals, whether or not incorporated in collars, shampoo agents, or the like, usually have a strong odor which is offensive to human beings. Conseqently, the animal which may have been trained and treated as an indoor animal, must remain in an outside environment for several days after the application of any insect repellent. In an effort to overcome the offensive odors to human beings some insect repellents have an odor countering agent, such as a perfume incorporated therein. However, these perfumes or other odor countering agents will mask or otherwise reduce the repellent ability and even to some extent the pesticidal activity.

Most of the commercially available repellents and shampoos use eucalyptus oil or eucalyptole, or various citric acid blends pennyroral and cedar oil as a primary ingredient. However, these repellents do not provide a strong repellent action and also provide effective pesticidal activity. Heretofore, there has not been any effective topically applied composition for reducing pest infestation or any shampoo agent for reducing pest infestation which does not have an offensive odor, which does not require periodic applications in relatively short time intervals and which is not an irritant to the animal. Further, there is not any composition of this type which is effective to repel and destroy pests when applied to human beings.

OBJECTS OF THE INVENTION

It is, therefore, a primary object of the present invention to provide a composition for reducing pest infestation of animals by topical application of the composition and which composition contains as its major ingredients, a eucalyptus oil, a low molecular weight and low carbon content alcohol and water.

It is another object of the present invention to provide a composition for reading pest infestation of the type stated in which the oil and the alcohol and the water are present in selected amounts to provide a highly effective pest repellent for use with domesticated animals.

It is a further object of the present invention to provide a composition of the type stated which does not act as an irritant to an animal when applied to the animal coat in proper amounts.

It is an additional object of the present invention to provide a composition of the type stated which includes eucalyptus oil as a pest repellent and a low molecular weight alcohol as a pesticide.

It is also an object of the present invention to provide a composition of the type stated which also includes relatively minor amounts of one or more low molecular weight aldehydes.

It is yet another object of the present invention to provide a composition of the type stated which can be adapted for topical application directly, or which can be topically applied in the form of a shampoo composition.

It is another salient object of the present invention to provide a method of reducing pest infestation of a domesticated animal by topically applying to the animal on a periodic basis a selected amount of a pest repellent composition based on and including the composition of the present invention.

It is still another object of the present invention to provide a method of improving a shampoo agent to provide highly effective pest repellent properties in the agent and where the shampoo leaves an effective pest repellent on the surface of the animal even when the shampoo is washed therefrom and which shampoo includes the composition of the present invention.

It is still a further object of the present invention to provide a composition of the type stated and a method of use in which the residue left on the animal after topical application is pleasant smelling and is completely devoid of the objectional odors normally associated with most insect repellents.

It is yet an additional object of the present invention to provide a composition which can be topically applied to human beings and which is effective as a pesticide and a pest repellent and which is not harmful to the human being.

With the above and other objects in view, my invention resides in the novel features of form, arrangement, and combination of components included in the composition and the method of improving a shampoo agent as well as in a method of reducing pest infestation, as hereinafter described in more detail. Thus, these and other objects will become apparent from the following description of the invention as embodied in this specification and the accompanying claims.

BRIEF SUMMARY OF THE DISCLOSURE

A composition for reducing pest infestation of domesticated animals after topical application thereof. The composition operates as a pesticide and as a pest repellent, but does not have the adverse condequences as do prior art pesticide compositions when applied to animals and even human beings.

The composition comprises, in a broad aspect, at least three major ingredients. The first of these ingredients is a eucalyptus oil and which may include a selected amount of eucalyptole. This eucalyptus oil is present in an amount of about 4% to about 22% by weight based on the total fluid weight of the composition. The second major ingredient is a low molecular weight and low carbon content alcohol which is miscible with water and is also present in an amount of about 9% to about 33% by weight based on the total fluid weight of the composition. Finally, as a third major ingredient, water is present in an amount of about 45% to about 85% by weight based on the total fluid weight of the composition.

In a more preferred embodiment of the invention, the oil is present in an amount of about 6% by weight to about 18% by weight, based on the total fluid weight of the composition. The low molecular weight alcohol is present in an amount of about 10% to about 26% by weight, based on the total fluid weight of the composition and the water is present in an amount of about 55% to about 85% by weight, based on the total fluid weight of the composition.

In a preferred embodiment, the low molecular weight alcohol is preferably isopropyl alcohol which may range from about 30% to about 90% alcohol content. In a more preferred embodiment a 90% isopropyl alcohol is employed. However, the alcohol can be selected from a class consisting of the methanol, ethanol, normal propyl and isopropyl alcohols, and the butyl alcohols, such as normal butyl alcohol, tertiary butyl alcohol and isobutyl alcohol.

In another preferred aspect of the invention, a minor amount of pinene is present in the composition and also, preferably one lower molecular weight aldehyde is present in the composition. The lower molecular weight aldehydes are preferably selected from the class consisting of capronaldehyde, valeraldehyde and butyraldehyde and mixtures of these three aldehydes.

As indicated previously, the compositions can be used for topical application directly, or they can be topically applied in the form of shampoo. The shampoo itself would include the aforesaid composition as well as the soap lathering agent selected from the class consisting of a stearate compound and a sulfate compound. More preferably, the sulfate compound would be a sodium sulfate and the stearate would be a sodium stearate. This compound would normally be present in an amount of about 15% to about 35% by weight, based on the total fluid weight of the composition.

In another preferred aspect of the invention, the composition can be mixed directly with a conventional animal shampoo in an amount of about 5% to about 20% by weight of the composition with respect to the total weight of the mixture of the composition and the shampoo. More preferably, the composition is present in an amount of about 10% by weight of the composition with respect to the total weight of the mixture of the composition and shampoo.

The present invention also provides a method of reducing pest infestation of domesticated animals by topically applying to the animal on a periodic basis a selected amount of the pest repellent composition. This pest repellent composition is that previously described. In like manner, the invention also comprises a method of improving a shampoo agent to provide a composition with highly effective pest repellent properties and where the shampoo agent leaves an effective pest repellent on the animal even when the shampoo has been washed therefrom.

The present invention has been found to be highly effective in substantially completely eliminating all pest infestation in smaller domesticated animals such as dogs and cats after essentially one application. The composition whether in a spray or a shampoo, can be used on animals of essentially all sizes and weights. When typically applied the composition remains effective as a repellent for up to seven days. In all concentration ranges specified herein the composition remains effective. With larger domesticated animals, the periods between application may be slightly shorter to obtain complete pest elimination. When the composition is applied to the animal, the pesticidal activity begins almost immediately and will essentially destroy all pests in about three to four seconds. Further, in all cases, there is no noticeable irritation to the skin of the animal and no adverse effects to the coat of the animal.

This invention possesses many other advantages and has other purposes which may be made more clearly apparent from a consideration of forms in which it may be embodied. These forms are described in the present specification and in the examples accompanying and forming part of the present specification. They will now be described in detail, for the purposes of illustrating the general principles of the invention; but it is to be understood that such detailed descriptions are not to be taken in a limiting sense.

DETAILED DESCRIPTION OF PREFERRED EMBODIMENTS

The present invention is based on a surprising discovery that a eucalyptus oil and a low molecular weight low carbon content alcohol and water can be mixed to provide a composition which is highly effective in reducing pest infestation. The eucalyptus oil which is employed is preferably, although not necessarily, derived from dried leaves of an Eucalyptus globulus.

The term "pest infestation" as used herein is deemed to include infestation by all known forms of animal pests, such as fleas, ticks, mosquitos, lice, ear mites, lice and includes other insect forms, such as common flies, bees and wasps and other forms of pests, and including microbial pests. Furthermore, the composition of the invention when topically applied to domesticated animals appears to improve the health condition of the animal and to provide a luster to the fur of the animal. More importantly, this composition does not appear to be an irritant to the animal, as hereinafter described in more detail.

The compositions of the invention were designed for and highly effective for use on essentially all forms of animals, particularly domesticated animals, such as dogs, cats and the like. Indeed, the composition of the present invention are also highly effective when applied to human beings for repelling the same types of pests and particularly fleas and mosquitos. Thus, the term "animal" as used herein is used to the broad sense to include essentially all forms of animals which are capable of being domesticated as well as human beings.

Approximately 4.4% to about 22% of the eucalyptus oil by weight is mixed with about 9% to about 33% by weight of a low molecular weight low carbon content alcohol. The alcohols which can be used have been described above, although as indicated, isopropyl alcohol (90%) is one of the preferred alcohols in accordance with the present invention. Finally, and in a broad aspect, water makes up the remainder of the composition and is generally present in an amount of about 45% to about 85% by weight based on the total fluid weight of the composition. In the composition the eucalyptus oil and the alcohol can exist in about equal amounts.

As indicated previously, the alcohols which are used are essentially all low molecular weight alcohols with low carbon contents, as for example, 1 to 5 or 6 carbon atoms. Further, the alcohols can range in percent strengths from 40% to about 95% percent alcohol content. In one of the preferred embodiments, isopropyl alcohol of 90% concentration is employed. However, in the case of pest repellent and pesticidal compositions for dogs and cats, it has been found that isopropyl alcohol of a 70% concentration rate is also highly effective.

In a more preferred embodiment, the oil is present in an amount of about 6% to about 18% by weight, based on the total fluid weight of the composition. The low molecular weight alcohol, such as isopropyl alcohol, is present in an amount of about 10% to about 26% by weight, based on the total fluid weight of the composition and water is generally present in an amount of about 55% to about 85% by weight, based on the total fluid weight of the composition.

The eucalyptus oil used in the present invention is usually about 70% to about 80% pure eucalyptus oil. In most embodiments a 78% composition is employed. For the purposes of this invention when the percentage of the components in the compositions are specified by weight or in percent amounts, it is to be understood that the eucalyptus oil is present in about a 70% to 80% pure condition and preferably a 78% pure condition.

As indicated previously, it has also been found that the presence of a minor amount of pinene, particularly in combination with the presence of a minor amount of a low molecular weight aldehyde, as hereinafter described, also adds beneficial results. The term "minor amount" with reference to the pinene and with reference to a low molecular weight aldehyde generally means 10% or less by weight based on the total weight of the composition, and more preferably 5% or less by weight, based on the total weight of the composition. Those aldehydes which have been found to be particularly effective in the present invention are capronaldehyde, valeraldehyde and butyraldehyde.

While the alcohol and the water are miscible, the eucalyptus oil is soluble in the alcohol but generally insoluble in the water. Consequently, and in many cases, there may be a phase separation after the composition stands for a relatively short period of time, as for example, about two minutes. Thus, it may be necessary to shake the composition slightly in order to at least obtain a homogeneous mixture of all of the ingredients prior to use. The composition of the invention can be generally applied at periodic intervals, as for example, about once each week. The composition can actually be applied with a small hand towel or wash rag to the coat of the animal. In like manner, the composition can be packaged as a spray repellent. However, when applied as a spray, or if applied by hand e.g. by a cloth, the effective repellent period is approximately 4 days requiring a new application thereafter.

In another aspect of the invention, the composition can be provided with a lathering agent to function as a shampoo, or otherwise it can be mixed with a conventional shampoo of the type which is not poisionous to or an irritant to the animal. In either case, the composition is highly effective when applied as a shampoo and washed from the animal to leave the remaining eucalyptus oil odor and which again is highly effective in repelling insects for a substantial period of time.

In one embodiment, a soap lathering agent, as for example, a stearate compound or a sulfate compound can be added to the composition. Preferably, sodium sulfate or sodium stearate or mixtures thereof can be added to the compound to provide a shampoo type action. When added, the sulfate or stearate compound is present in an amount of about 15% to about 35% by weight based on the total weight of the composition. Further, in an embodiment where the composition is added to a conventional shampoo agent, the composition is added so that it is present in an amount of about 5% to about 20% by weight and preferably about 10% by weight of composition with respect to the total weight of the mixture of composition and shampoo.

The compositions of the present invention are also highly effective as a pest repellent and pesticide, such as an insect repellent and pesticide when used with human beings. In the latter embodiment, it is preferable to use an alcohol such as ethyl alcohol, as opposed to isopropyl alcohol. One particularly effective alcohol is that known as S.D.A. 40-2 which is a perfume grade denatured alcohol primarily comprised of ethyl alcohol and having a formula of $C_2H_5OH$. This perfume grade alcohol is preferably 190 proof.

In a preferred embodiment when the composition is used for human being application, approximately one ounce of eucalyptus oil and one ounce of the alcohol along with six ounces of the water is employed. However, it is possible to use as much as one-half ounce of eucalyptus oil with respect to the alcohol and as much as one and one-half ounces of the eucalyptus oil with respect to one ounce of the alcohol.

The above composition designed for human application may also be applied to clothing with the exception of silk garments or garments containing silk. Further, the same bottling requirements will still apply with compositions designed for human application as those designed for animal pest application.

The time effectiveness as a pesticide and repellent on human beings is substantially less than in the case of other animals such as dogs and cats. In human beings, the compositions should be typically applied once every one to one and three fourths hours. This time may vary depending on the body chemistry of an individual, e.g. the degrees of which such human being may sweat. In regions of higher humidity only one application every two to three hours is required.

The present invention has been found to provide unexpected and yet exceptional properties in reducing, if not completely eliminating, pest infestation and particularly parasitic pest infestation. Recognizing that the eucalyptus oil is immiscible with water and only miscible with alcohol, one would not have expected a composition comprised of both water and alcohol and the eucalyptus oil to be effective. Even moreso, significantly greater beneficial results and efficacy were obtained when a minor amount of pinene and a minor amount of one of the low molecular weight aldehydes specified herein was included in the composition. The exact interaction of the pinene and low molecular weight aldehyde is not necessarily understood, although it is known to provide highly effective results.

The present invention is effective in repelling insects and other pest forms by the eucalyptus oil. Further, and to insure a complete absence of pest infestation the low molecular weight alcohol acts as a pesticide. Both components are selected and the amounts are properly proportioned so as to ensure against adverse affects to the animal.

The compositions of the invention can also have a coloring agent included therein for purposes of aesthetics. However, coloring agents are not necessary. For that matter, other agents of the type normally found in shampoos and the like could be added, if desired.

The eucalyptus oil containing compositions of the invention should be stored in high density polyvinylchloride bottles. Furthermore, these bottles should be of the shiny white type, as opposed to the dull white high density polyethylene to prevent glazing of the bottles.

Extensive field studies were conducted with the composition of the present invention in both controlled and non-controlled environments. Test results revealed that in non-controlled flea infested areas, the repellent effectively erradicated and repelled fleas and mosquitos for up to four consecutive days. These tests also revealed that in a controlled environment, such as an indoor environment with a front and back yard which is professionally treated by an exterminator, all animals had the same results, namely there were no fleas or mosquitos, or lice, or ear mites, for four days when the animals were sprayed with the composition as a repellent. When a shampoo using the composition, hereinafter described, was employed, fleas, mosquitos, lice and ear mites were also effectively erradicated and repelled for four consecutive days. When the animals were washed with a shampoo using the composition, repelling action and pesticidal activity lasted four days and with spraying thereafter, repelling action and pesticidal activity was increased for four additional consecutive days or a total of eight consecutive days. The same applications took place for a period of six months and further testing provided the same results.

While the compositions of the invention do not necessarily kill eggs of these pests, the compositions were found to be effective in precluding pest eggs from sticking to the animal fur. In this way, after a simple spraying or washing with the shampoo containing the composition, the eggs were effectively removed by washing. While the commercially available repellents do not effectively remove eggs, even though they may contain claims to the contrary, the composition of the present invention is at least more effective in enabling the removal of the eggs by washing.

Of significant importance is the fact that in all animals, there was no irritation to the skin of the animal and in fact, it was found that the composition appeared to aid in healing of irritated skin from any previous flea and mosquito bites. In addition, the composition in spray form did not appear to be a severe eye irritant to the animal, although in a shampoo form eye irritation does occur and care should be exercised in avoiding contact with sensitive areas, such as the eyes. Further, the composition actually provided a luster to the fur coat of the animal and provided a rather silky touch to the animal. The composition, when applied and thereafter dried, was non-greasy and the animal hair or fur was easy to comb. Finally, the animals, including smaller domesticated animals, such as dogs, cats, puppies and kittens showed no adverse side effects from the applied composition.

The only residue which remained on the animal hair or fur is the eucalyptus oil which is essentially pleasent smelling and acts as a natural repellent against known forms of animal pests. In addition, the composition can be stored at room temperature for long periods of time without reducing the efficacy of the composition.

EXAMPLES OF USE

The following examples are illustrative of the principles of the invention, but it is to be understood that these examples are not deemed to be non-limiting to the invention.

EXAMPLE 1

A mixture of one ounce of pure eucalyptus oil and about two ounces of isopropyl alcohol (at least 90%) were added to thirteen ounces of water and the composition is throughly mixed. The composition included approximately 6% of oil by weight and approximately 12% of the alcohol by weight and approximately 82% of water by weight, based on the total fluid weight of the composition. The composition, when tested proved to be highly effective as a topically applied agent for reducing pest infestation. Further, this composition proved to be highly effective as a shampoo when incorporated in a conventional shampoo agent.

EXAMPLE 2

To the composition of Example 1, sodium sulfate was added in an amount of about one ounce. Benzyl alcohol was also added in an amount of about 0.5 ounce and a D and C yellow dye number 10 and a D and C yellow dye number 6 were also added to the composition in amounts only to change the color thereof. Here again, it was noted that the same beneficial results were achieved as with the composition of Example 1.

EXAMPLE 3

A mixture approximately 25% by weight of isopropyl alcohol and about 18.75% by weight of eucalyptus oil was made along with about 56.25% of distilled water. The composition was tested and found to be highly effective as a spray. The composition had a specific gravity of about 0.9324 and a pH of about 4.37. Further, the composition had a viscosity of about one poise.

EXAMPLE 4

Approximately one and one-half ounces of eucalyptus oil in and two ounces of isopropyl alcohol were mixed with four and one-half ounces of water to provide a topical application agent with insect repellent properties. This repellent yielded about 18% oil, by weight with respect to the total fluid weight of the composition, approximately 25% by weight of alcohol with respect to the total weight of the composition and approximately 63% by weight of water with respect to the total weight of the composition. This composition is highly effective as a spray.

Due to the increased amount of alcohol and eucalyptus oil, this composition is found to be superior with respect to larger animals, such as domesticated horses and the like, whereas the composition of Example 1 is found to be highly effective with smaller domesticated animals, such as dogs, cats and the like.

EXAMPLE 5

In order to produce a shampoo agent for topical application to an animal for purposes of washing the animal, approximately four ounces of eucalyptus oil were mixed with about four ounces of isopropyl alcohol (90%) and about four ounces of sodium sulfate were added to about sixteen ounces of water. The total composition weighed about twenty eight fluid ounces. This composition resulted in an oil present in an amount of about 14% by weight, the alcohol present in an amount of about 14% by weight and the sodium sulfate present in an amount of about 14% be weight with water being present in an amount of about 58% by weight.

This composition was also found to be effective when used as a shampoo for washing smaller domesticated animals. With one washing of the shampoo liberally applied, it is found that fleas, ticks, mosquitoes and ear mites were repelled for at least about three to four days in non-controlled environments. In controlled environments, the repellent and pesticide activity was found to be present for up to an additional three days.

EXAMPLE 6

The composition of Example 5 is mixed with about ten ounces of a conventional shampoo agent of the type normally used for domesticated animals. Approximately one ounce of the composition is mixed with about ten ounces of the shampoo. This shampoo when applied to domesticated animals is also found to be highly effective. Here again, with one washing of the animal with the shampoo and rinsing of the resulting lather therefrom, the remaining eucalyptus oil scent provides effective flea and tick repelling action against fleas, ticks, mosquitos and ear mites for at least three to four days in non-controlled environments. In controlled environments, which have been sprayed with a pesticide, the use of a shampoo composition of the invention shows a continuous repellent activity for up to seven days with one application.

EXAMPLE 7

The shampoo composition of Example 6 is used to wash cats in order to determine the effect in flea and mosquito repelling action. The tests are conducted in non-controlled flea-infested areas. When the cats are washed with the shampoo agent of Example 6, it is found that fleas, ticks, mosquitos and ear mites are effectively repelled for up to four consecutive days. When the composition of Example 1 is applied topically at the fourth day, it is found that three additional consecutive days of highly effective repelling action against fleas, ticks, mosquitos and ear mites are also obtained.

EXAMPLE 8

The tests of Example 7 are also repeated in a controlled front yard and backyard environment with regard to indoor cats. All of the indoor cats in this example are subjected to the same treatment as the cats in Example 7. It is found that the fleas, mosquitos, ticks and ear mites will not bite or infest an animal when washed with the shampoo for at least about four days and when further treated with the agent of Example 1, on about the fourth day for an additional three day period.

EXAMPLE 9

The following example describes a composition which has been made and found to be highly effective for use as a topical applicant to human beings to act as an insect repellent and pesticide. Approximately one ounce of eucalyptus oil is mixed with about one ounce of S.D.A. 40-2 alcohol which is primarily a denatured ethyl alcohol and six ounces of purified water. The resultant composition has aproximately 12½% of eucalyptus oil and 12½% of the alcohol and approximately 75% of water.

This composition is found to be highly effective in repelling insects and the like pests from human beings in noncontrolled environments.

EXAMPLE 10

The compositions of the invention in the form of a shampoo were tested to determine the effect on the eyes of small animals such as rabbits. The composition of Example 1 was mixed with a conventional shampoo to provide a shampoo agent used for this purpose. 0.1 ml. of this test material was placed into the left eye of each of nine rabbits and six of the animals were without washout and the eyes of three of the animals were subsequently washed out with water. The test results are set forth in the following table:

|  | Time after instillation | | | | Highest Mean Score |
|---|---|---|---|---|---|
|  | 24 hr | 48 hr | 72 hr | 7 days |  |
|  | Mean Scores | | | | |
| No Washout | 7.0 | 8.0 | 8.7 | 1.67 | 8.7 |
| With Washout | 2.0 | 0 | 0 | 0 | 2.0 |
|  | No. of rabbits with positive reactions | | | | |
| No Washout | 2 | 2 | 2 | 2 |  |
| With Washout | 0 | 0 | 0 | 0 |  |

After about 24 hours, two of the rabbits, where no washout occurred, exhibited positive reaction. Irritation occured in the cornea, iris and conjunctivae. Slight conjunctivitis was noted in two additional animals whose eyes were not washed out. After about 48 hours, slight conjunctivitis had subsided but other positive reactions remain the same. By the end of the 7th day, all irritation to the iris and conjunctivae had subsided. Moderate corneal damage did remain in two of the 5 animals. For those eyes which were washed, after about 24 hours, 2 of the animals displayed slight conjunctivitis. After about 48 hours, no damage of any type was observed in these animals.

The grading scale for ocular reaction is as follows:

| 1. | Cornea | |
|---|---|---|
| A. | Opacity - degree of density (area most dense taken for reading) | |
| | No opacity | 0 |
| | Scattered or diffuse areas, details of iris slightly obscured | 1 |
| | Easily discernible translucent areas, details of iris slightly obscured | 2 |
| | Opalescent areas, no details of iris visible, size of pupil barely discernible | 3 |
| | Opaque, iris visible | 4 |
| B. | Area of cornea involved | |
| | One quarter or less, but not zero | 1 |
| | Greater than one quarter, but less than half | 2 |
| | Greater than half, but less than three quarters | 3 |
| | Greater than three quarters, up to whole area | 4 |
| 2. | Iris | |
| A. | Values | |
| | Normal | 0 |
| | Folds above normal, congestion, swelling circumcorneal injection (any or all of these or combination of any thereof) iris still reacting to light (sluggish reaction to positive) | 1 |
| | No reaction to light, hemmorage, gross destruction (any or all of these) | 2 |

The maximum cornea score for this test is 80. The maximum iris score is 10.

| 3. | Conjunctivae | |
|---|---|---|
| A. | Redness | |
| | Vessels normal | 0 |
| | Vessels definitely injected above normal | 1 |
| | More diffuse, deeper crimson red, individual vessels not easily descernible | 2 |
| | Diffuse beefy red | 3 |
| B. | Chemosis | |
| | No swelling | 0 |
| | Any swelling above normal (includes nictiating membrane) | 1 |
| | Obvious swelling with partial eversion of lids | 2 |
| | Swelling with lids about half closed | 3 |
| | Swelling with lids half closed to completely closed | 4 |
| C. | Discharge | |
| | No discharge | 0 |
| | Any amount different from normal (does not include small amounts observed in inner canthus of normal animals) | 1 |
| | Discharge with moistening of lids and hairs just adjacent to lids | 2 |
| | Discharge with moistening of the lids and hairs, and considerable area around the eye | 3 |

The maximum conjunctivae score is 20. The total score for the eye is the sum of all scores obtained for the cornea, iris and conjunctivae. The maximum ocular score is 110. The total mean score was obtained by dividing the mean scores for all animals at 24 hours, 48 hours, and 72 hours.

The following table sets forth the irritation means scores along with the definitions of these mean scores:

| Rating | Range of Mean Scores | Definition |
|---|---|---|
| Non-irritating | 0.0–0.5 | To maintain this rating, all scores at the 48-hour reading must be zero; otherwise, increase rating one level. |
| Practically Non-irritating | 0.6–2.5 | To maintain this rating, all scores at the 48-hour reading must be zero; otherwise, increase rating one level. |
| Minimally irritating | 2.5–15.0 | To maintain this rating, all scores at the 72-hour reading must be zero; otherwise, increase rating one level. |
| Mildly irritating | 16.0–25.0 | To maintain this rating, all scores at 7-day reading must be zero; otherwise, increase rating one level. |
| Moderately irritating | 26.0–50.0 | To maintain this rating, scores at 7-day must be less than or equal to 10 for 60% or more of the animals. Also, the mean 7-day score must be less than or equal to 20. If the 7-day mean score is less than or equal to 20 and more than 60% of animals show scores less than 10, then no animal among those showing scores greater than 10 can exceed a score of 30 if rating is to be maintained; otherwise, increase the rating one level |
| Severely irritating | 51.0–80.0 | To maintain this rating, scores at 7-day must be less than or equal to 30 for 60% or more of the animals. Also, if the mean 7-day score is less than or equal to 40 and more than 60% of the animals show scores less than or equal to 30, then no animal among these showing scores greater than 30 can exceed a score of 60 if rating is to be maintained; otherwise increase the rating one level. |
| Extremely irritating | 81.0–110.0 | |

The mean score for a rating is taken from observation time which has the highest mean score. Where responses are persistent, the rating is increased by only one level.

EXAMPLE 11

The shampoo used in Example 10 was employed in a primary dermal irritancy test. This shampoo was topically applied to six of the rabbits referred to in Example 10. 0.5 mililiter of a sample was topically applied to a test area on each of the animals. The following test results were obtained:

| | 24 hours | | 72 hours | |
|---|---|---|---|---|
| Rabbit # | Intact | Abraded | Intact | Abraded |
| | ERYTHEMA-ESCHAR | | | |

-continued

| Rabbit # | 24 hours | | 72 hours | |
| --- | --- | --- | --- | --- |
| | Intact | Abraded | Intact | Abraded |
| 1 | 1 | 1 | 1 | 0 |
| 2 | 0 | 1 | 0 | 0 |
| 3 | 1 | 2 | 0 | 1 |
| 4 | 0 | 0 | 0 | 0 |
| 5 | 0 | 1 | 0 | 0 |
| 6 | 1 | 1 | 1 | 0 |
| Mean Score: | 0.5 | 1.0 | 0.33 | 0.17 |
| EDEMA | | | | |
| 1 | 0 | 0 | 0 | 0 |
| 2 | 0 | 0 | 0 | 0 |
| 3 | 0 | 0 | 0 | 0 |
| 4 | 0 | 0 | 0 | 0 |
| 5 | 0 | 0 | 0 | 0 |
| 6 | 0 | 0 | 0 | 0 |
| Mean Score: | 0 | 0 | 0.17 | 0 |

The primary irritation score was 0.54. The sample according to the definition again in Title 16, Code of Federal Regulations, Section 1500.3 was found not to be a primary irritant.

The following values were used in the evaluation of the skin reactions for the above test results set forth in this Example 11.

| EVALUATION OF SKIN REACTIONS | |
| --- | --- |
| Erythema and Eschar Formation | Value |
| No erythema | 0 |
| Very slight erythema (barely perceptible) | 1 |
| Well-defined erythema | 2 |
| Moderate to severe erythema | 3 |
| Severe erythema (beet redness) to slight eschar formation (injuries in depth) | 4 |

| Edema Formation | Value |
| --- | --- |
| No edema | 0 |
| Very slight edema (barely perceptible) | 1 |
| Slight edema (edges of area well defined by definite raising) | 2 |
| Moderate edema (raised approximately 1 mm) | 3 |
| Severe edema (raised more than 1 mm and extending beyond the area of exposure) | 4 |

| PRIMARY IRRITATION SCORE | DESCRIPTIVE RATING |
| --- | --- |
| 0 | Non-irritating |
| 0.1–0.5 | Minimally irritating |
| 0.6–2.0 | Slightly irritating |
| 2.1–5.0 | Moderately irritating |
| 5.1–6.5 | Severely irritating |
| 6.6–8.0 | Extremely irritating |

A score of 5 or more is considered to be a failing score.

EXAMPLE 12

The composition of Example 1 also in the form of a shampoo was also tested for acute oral toxicity in a single dose. That shampoo composition prepared in accordance with Example 10 was employed for this purpose.

The acute single dose oral toxicity test was performed on Sprague-Dawley rats with an objective to establish an apparent $LD_{50}$ of greater than 5 grams per kilogram. Ten Sprague-Dawley rats were fed a dosage of 5 grams per kilogram of body weight by oral intubation and thereafter fed a balanced diet of rat pellets and water ad libitum. Then additional rats of the same strain, serving as controls, were fed an equivalent amount of water by the same route as the test rats. All animals received a balanced diet or rat pellets and water ad libitum. The rats were examined after two (2) hours and for fourteen (14) days. Initial and final weights, and toxic symptoms were recorded. Necropsies were performed on all expired animals and a minimum of 20% of survivors.

All animals were acclimated for a minimum of five days and checked carefully prior to testing. The animals were housed in stainless steel suspended cages. The room in which the animals were housed received a minimum of ten complete air exchanges every hour. The photo period was twelve hours light and twelve hours darkness. The ambient temperature range was about 74 to 76 degrees F. The following generally provides an interpretation of the test results. The test material passes the acute oral toxicity test at the single dosage utilized if fewer than 50% of the rats died. The following test results are set forth:

Two (2) animals expired during the duration of the test.

| Mean Weight Gain | At 7 days | At 14 days |
| --- | --- | --- |
| Test females: | 17.4 | 24.2 |
| Test males: | 30.4 | 54.4 |
| Control females: | 19.2 | 25.8 |
| Control males: | 63.0 | 78.0 |

Toxicological Summary

One rat had expired within two hours of intubation. Others exhibited malaise and catatonia. At twenty-four hours one animal was found dead. Toxicological observations included piloerection, muscular weakness, micturation, diarrhea and passive behavior. At forty-eight hours animals had improved displaying only piloerection and passive behavior. All animals remained in this condition throughout a period of four days. By seven days all surviving animals appeared normal.

Pathology Summary

Upon necropsy of expired and sacrificed animals, one abnormality was found. The gastrointestinal tract appeared hemorrhagic in nearly all animals. All other findings were normal.

Conclusions The sample has an oral $LD_{50}$ of greater than 5 g/kg and may not be defined as "Toxic" according to the Code of Federal Regulations, Title 16, Sec. 1500.3.

EXAMPLE 13

The compositions of the invention in the form of a repellent spray were also tested to determine the effect on the eyes of small animals, such as rabits. For these tests the composition of Example 4 was used.

0.1 ml of the test material was placed into the left eye of nine rabbits. Three of the animals had their eyes washed out and six of the animals did not have their eyes washed out. The test results are set forth in the following table:

|  | Time after instillation | | | | Highest |
| --- | --- | --- | --- | --- | --- |
|  | 24 hr. | 48 hr. | 72 hr. | 7 days | Mean Score |
|  | Mean Scores | | | | |
| No Washout | 16.67 | 21.5 | 18.17 | 9.17 | 21.5 |
| With Washout | 8.33 | 17.0 | 9.0 | 1.67 | 17.0 |
|  | No. of rabbits with positive reactions | | | | |
|  | 4 | 2 | 2 | 2 | |
|  | 1 | 1 | 1 | 1 | |

With the six animals where no washout occured, after about twenty-four hours four rabbits demonstrated positive reactions. Three rabbits exhibited corneal irritation and all of the rabbits displayed some conjunctival disorder. After about forty-eight hours two rabbits exhibited corneal irritation and iritis and five rabbits displayed conjunctival damage. After about seventy-two hours two rabbits still revealed corneal irritation and iritis and three rabbits displayed conjunctival damage. After seven days two positive reactors remained, exhibiting corneal and conjunctival irritation and iritis.

With the three animals where washout did occur, after about twenty-four hours one animal exhibited corneal irritation and two rabbits displayed conjunctival irritation. After about forty-eight hours corneal damage, iritis, and conjunctival irritation was found in one rabbit. The readings were the same at about seventy-two hours. After seven days iritis and conjunctival irritation had subsided but corneal damages was still present in one animal.

EXAMPLE 14

The sample of Example 4 was used in order to determine primary dermal irritancy with a repellent spray. 0.5 mililiters of the sample were applied to six rabbits. The following test results were obtained:

| Rabbit # | 24 hours | | 72 hours | |
| --- | --- | --- | --- | --- |
|  | Intact | Abraded | Intact | Abraded |
|  | ERYTHEMA-ESCHAR | | | |
| 1 | 1 | 1 | 0 | 0 |
| 2 | 1 | 1 | 1 | 0 |
| 3 | 0 | 0 | 0 | 0 |
| 4 | 1 | 0 | 0 | 0 |
| 5 | 0 | 0 | 0 | 0 |
| 6 | 1 | 1 | 0 | 0 |
| Mean Score: | 0.83 | 0.5 | 0.17 | 0 |
|  | EDEMA | | | |
| 1 | 0 | 0 | 0 | 0 |
| 2 | 0 | 0 | 0 | 0 |
| 3 | 0 | 0 | 0 | 0 |
| 4 | 0 | 0 | 0 | 0 |
| 5 | 0 | 0 | 0 | 0 |
| 6 | 0 | 0 | 0 | 0 |
| Mean Score: | 0 | 0 | 0 | 0 |

The primary irritation score was 0.38. This sample according to the definition in Title 16, Code of Federal Regulations, Section 1500.3 was found to be not a primary irritant.

The following values were used in the evaluation of the skin reactions for the above test results set forth in this Example 14.

| EVALUATION OF SKIN REACTIONS | |
| --- | --- |
| Erythema and Eschar Formation | Value |
| No erythema | 0 |
| Very slight erythema (barely perceptible) | 1 |
| Well-defined erythema | 2 |
| Moderate to severe erythema | 3 |
| Severe erythema (beet redness) to slight eschar formation (injuries in depth) | 4 |
| Edema Formation | Value |
| No edema | 0 |
| Very slight edema (barely perceptible) | 1 |
| Slight edema (edges of area well defined by definite raising) | 2 |
| Moderate edema (raised approximately 1 mm) | 3 |
| Severe edema (raised more than 1 mm and extending beyond the area of exposure) | 4 |

| PRIMARY IRRITATION SCORE | DESCRIPTIVE RATING |
| --- | --- |
| 0 | Non-irritating |
| 0.1–0.5 | Minimally irritating |
| 0.6–2.0 | Slightly irritating |
| 2.1–5.0 | Moderately irritating |
| 5.1–6.5 | Severely irritating |
| 6.6–8.0 | Extremely irritating |

A score of 5 or more is considered to be a failing score.

EXAMPLE 15

The composition of Example 4 also in the form of a repellent spray was also tested for acute oral toxicity in a single dose.

The acute single dose oral toxicity test was performed on Sprague-Dawley rats with an objective to establish an apparent $LD_{50}$ of greater than 5 grams per kilogram. Ten Sprague-Dawley rats were fed a dosage of 5 grams per kilogram of body weight by oral intubation and thereafter fed a balanced diet of rat pellets and water ad libitum. Then additional rats of the same strain, serving as controls, were fed an equivalent amount of water by the same route as the test rats. All animals received a balanced diet or rat pellets and water ad libitum. The rats were examined after two (2) hours and for fourteen (14) days. Initial and final weights, and toxic symptoms were recorded. Necropsies were performed on all expired animals and a minimum of 20% of survivors.

All animals were acclimated for a minimum of five days and checked carefully prior to testing. The animals were housed in stainless steel suspended cages. The room in which the animals were housed received a minimum of ten complete air exchanges every hour. The photo period was twelve hours light and twelve hours darkness. The ambient temperature range was about 74 to 76 degrees F. The following generally provides an interpretation of the test results. The test material passes the acute oral toxicity test at the single dosage utilized if fewer than 50% of the rats died. The following test results are set forth:

Four (4) animals expired during the duration of the test.

| Mean Weight Gain | At 7 days | At 14 days |
| --- | --- | --- |
| Test females: | 7.8 | 15.8 |

-continued

| Mean Weight Gain | At 7 days | At 14 days |
|---|---|---|
| Test males: | 15.6 | 35.8 |
| Control females: | 19.2 | 25.8 |
| Control males: | 63.0 | 78.0 |

Toxicological Summary

At twenty-four hours two animals were found dead. Toxicological observations included muscular weakness, dyspnea, lactimation, catatonia, absence of corneal reflex, piloerection and diarrhea. At forty-eight hours animals appeared to be in the same condition. Males had slightly improved. At seventy-two hours one other male rat had expired. Others seemed to improve displaying only piloerection, passive-fearful behavior and catatonia in one animal. At day seven all but one rat appeared normal. This one rat, a female rat, was found dead on day eight. Others remained normal throughout the fourteen days testing period.

Pathology Summary

Upon necropsy of the four expired animals, abnormalities were found in the heart, lungs and gastrointestinal tract. The lungs appeared pale, congested and hemorrhagic in two animals. The heart appeared normal in size and shape, but was very pale in color (occurred in one animal). In one animal the stomach was found distended with moderate hemorrhage and the intestines were found also to be slightly hemorrhagic.

All surviving animals appeared normal. No abnormalities were present in any of the control animals.

Conclusions

The sample has an oral $LD_{50}$ of greater than 5 g per kilogram and is considered "non-toxic" according to the Code of Federal Regulations, Title 16, Section 1500.3.

It has also been known that various forms of animal pests, and particularly parasite pests, such as fleas, ticks, lice and mites are responsible for various health disorders of animals, such as skin disorders which can cause intense itching, scratching, uncomfortable irritation and oftentimes results in secondary bacterial infection. Further, it has also been known that certain pests which are external parasites, such as the otodectes cynotis mite will produce ear damage in smaller animals and particularly in cats. This species will attack the ear and often penetrate the ear drum causing disequilibrium combined with bacterial infection and often result in deafness.

The present invention is highly effective in overcoming essentially all of these and other problems which are normally present in pest infestation and particular parasitic pest infestation. Thus, the present invention has not only been found to be highly effective in reducing and substantially eliminating pest infestation, but also in substantially improving the health of the animal and condition of the animals coat.

Thus there has been described a unique and novel pest repellent composition and method of controlling animal pest infestation which uses a eucalyptus oil, alcohol and water mixture and which thereby fulfills all of the objects and advantages which have been sought. It should be understood that many changes, modifications, variations and other uses and applications will become apparent to those skilled in the art after considering this specification. Therefore, any and all such changes, modifications, variations and other uses and applications which may become apparent to those skilled in the art after considering this specification are deemed to be covered by the invention which is limited only by the following claims.

Having thus described my invention, what I to claim and secure by Letters Patent is:

1. A composition for reducing flying insect pest infestation of animals and human beings with topical application thereof by exhibiting pest repellent activity and pesticidal activity, said composition comprising:
   (a) eucalyptus oil present in an amount of about 4% to about 22% by weight based on the total fluid weight of the composition,
   (b) a low molecular weight and low carbon content alcohol miscible with water and present in an amount of about 9% to about 33% by weight based on the total fluid weight of the composition to provide pesticidal activity, and
   (c) water present in an amount of about 45% to about 85% by weight based on the total fluid weight of the composition, and which composition contains the eucalyptus oil and alcohol in amounts to operate as an effective pest repellant pesticide and which does not become an animal or human irritant when used in a proper amount and regime.

2. The composition of claim 1 further characterized in that said low molecular weight alcohol is selected from the class consisting of methanol, ethanol, normal propyl and isopropyl alcohol and the butyl alcohols.

3. The composition of claim 1 further characterized in that said low molecular weight alcohol is isopropyl alcohol.

4. The composition of claim 1 further characterized in that said composition also comprises a minor amount of pinene and a minor amount of at least one low molecular weight aldehyde.

5. The composition of claim 1 further characterized in that said composition comprises a minor amount of pinene, and a minor amount of an aldehyde selected from the group consisting of capronaldehyde, valeraldehyde, and butyraldehyde, and mixtures of the foregoing.

6. The composition of claim 1 further characterized in that said oil is present in an amount of about 6% to about 18% by weight based on the total fluid weight of the composition, said low molecular weight alcohol is present in an amount of about 10% to about 26% by weight based on the total fluid weight of the composition, and the water is present in an amount of about 55% to about 85% by weight based on the total fluid weight of the composition.

7. The composition of claim 1 further characterized in that said composition is mixed with a conventional animal shampoo in amount of about 5% to about 20% by weight of composition with respect to the total weight of the mixture of composition and shampoo.

8. The composition of claim 1 further characterized in that said composition is mixed with a conventional animal shampoo in amount of about 10% by weight of composition with respect to the total weight of the mixture of composition and shampoo.

9. A method of reducing pest infestation of animals and human beings, said method comprising topically applying to said animal or human being on a periodic basis, a selected amount of a pest repellent composition which exhibits pest repellent activity and pesticidal activity, and wherein said composition is comprised of:
  (a) eucalyptus oil present in an amount of about 4% to about 22% by weight based on the total fluid weight of the composition,
  (b) a low molecular weight and low carbon content alcohol miscible with water and prsent in an amount of about 9% to about 33% by weight based on the total fluid weight of the composition, and
  (c) water present in an amount of about 45% to about 85% by weight based on the total fluid weight of the composition, and which composition contains the eucalyptus oil and alcohol in amounts to operate as an effective pest repellent and pesticide and which does not become an animal or human irritant when used in a proper amount and regime.

10. The method of claim 9 further characterized in that said method uses a composition in which the low molecular weight alcohol is selected from the class consisting of methanol, ethanol, normal propyl and isopropyl alcohol and the butyl alcohols.

11. The method of claim 10 further characterized in that the method uses a composition in which the composition comprises a minor amount of pinene and a minor amount of a low molecular weight aldehyde.

12. The method of claim 9 further characterized in that said method uses a composition in which the low molecular weight alcohol is isopropyl alcohol.

13. The method of claim 9 further characterized in that the method uses a composition in which the composition comprises a minor amount of pinene, and a minor amount of an aldehyde selected from the class consisting of capronaldehyde, valeraldehyde, and butyraldehyde, and mixtures of the foregoing.

14. The method of claim 9 further characterized in that said method uses a composition in which the oil is present in an amount of about 6% to about 18% by weight based on the total fluid weight of the composition, said low molecular weight alcohol is present in an amount of about 10% to about 26% by weight based on the total fluid weight of the composition, and the water is present in an amount of about 55% to about 85 by weight based on the total fluid weight of the composition.

15. The method of claim 9 further characterized in that said method comprises topically applying said composition by washing the animal with a shampoo mixture comprised of said composition which is mixed with a conventional animal shampoo in amount of about 5% to about 20% by weight of composition with respect to the total weight of the mixture of composition and shampoo.

16. The method of claim 9 further characterized in that said method comprises topically applying said composition by washing the animal with a shampoo mixture comprised of said composition which is mixed with a conventional animal shampoo in an amount of about 10% by weight of composition with respect to the total weight of the mixture of composition and shampoo.

17. A method of improving a shampoo agent to provide highly effective flying insect pest repellent properties and wherein the shampoo agent leaves an effective pest repellent on an animal or human being and provides effective pesticidal activity to the animal or human being when the agent is washed from the animal or human being, said method comprises adding to the shampoo agent a composition comprised of:
  (a) eucalyptus oil present in an amount of about 4% to about 22% by weight based on the total fluid weight of the composition,
  (b) a low molecular weight and low carbon content alcohol miscible with water and present in an amount of about 9% to about 33% by weight based on the total fluid weight of the composition, and
  (c) water present in an amount of about 45% to about 85% by weight based on the total fluid weight of the composition, and which composition contain the eucalyptus oil and alcohol in amounts to operate as an effective pest repellant and pesticide and which does not become an animal or human irritant when used in a proper amount and regime.

18. The method of improving a shampoo agent of claim 17 further characterized in that said method comprises adding to the shampoo agent a composition in which the low molecular weight alcohol is selected from the class consisting of methanol, ethanol, normal propyl and isopropyl alcohol and the butyl alcohols.

19. The method of improving a shampoo agent of claim 17 further characterized in that said method comprises adding to the shampoo agent a composition in which the low molecular weight alcohol is isopropyl alcohol.

20. The method of improving a shampoo agent of claim 17 further characterized in that said method comprises adding to the shampoo agent a composition in which the composition also comprises a minor amount of pinene, and a minor amount of at least one lower molecular weight aldehyde.

21. The method of improving a shampoo agent of claim 17 further characterized in that said method comprises adding to the shampoo agent a composition in which the composition also comprises a minor amount of pinene, and a minor amount of an aldehyde selected from the class consisting of capronaldehyde, valeraldehyde, and butyraldehyde and mixtures of the foregoing.

22. The method of improving a shampoo agent of claim 17 further characterized in that said method comprises adding to the shampoo agent a composition in which the oil is present in an amount of about 6% to about 18% by weight based on the total fluid weight of the composition, said low molecular weight alcohol is present in an amount of about 10% to about 26% by weight based on the total fluid weight of the composition, and the water is present in an amount of about 55 to about 85% by weight based on the total fluid weight of the composition.

23. A composition for reducing flying insect pest infestation of animals and human beings with topical application thereof by exhibiting pest repellent activity and pesticidal activity, said composition comprising:
  (a) eucalyptus oil present in an amount of about 4% to about 22% by weight based on the total fluid weight of the composition,
  (b) a low molecular weight and low carbon content alcohol miscible with water and selected from the class consisting of methanol, ethanol, normal propyl and isopropyl alcohols and the butyl alcohols, and where the alcohol is present in an amount of about 9% to about 33% by weight based on the total fluid weight of the composition,
  (c) water present in an amount of about 45% to about 85% by weight bused on the total fluid weight of the composition,
  (d) a minor amount of pinene, and (e) a minor amount of a low molecular weight aldehyde selected from the class consisting of capronaldehyde, valeraldehyde and butyraldehyde, and mixtures of such aldehydes, and which composition contains the eucalyptus oil and alcohol and the pinene and aldehyde in amounts to operate as an effective pest repellent and pesticide and which does not become an animal or human irritant when used in a proper amount and regime.

24. The composition of claim 23 further characterized in that said composition is mixed with a conventional animal shampoo in an amount of about 5% to about 20% by weight of composition with respect to the total weight of the mixture of composition and shampoo.

* * * * *